United States Patent
Shamanin et al.

(10) Patent No.: US 6,368,832 B1
(45) Date of Patent: Apr. 9, 2002

(54) PAPILLOMA VIRUSES, AGENTS FOR DETECTING THEM AND FOR TREATING DISEASES CAUSED BY SUCH VIRUSES

(75) Inventors: Vladimir Shamanin, Heidelberg; Ethel-Michele De Villiers-Zur Hausen; Harald Zur Hausen, both of Waldmichelbach, all of (DE)

(73) Assignee: Deutsches Krebsforschungszentrum Stiftung des Öffentlichen Rechts, Heidelberg (DE)

( * ) Notice: Subject to any disclaimer, the term of this patent is extended or adjusted under 35 U.S.C. 154(b) by 0 days.

(21) Appl. No.: 09/628,099

(22) Filed: May 25, 2000

Related U.S. Application Data

(62) Division of application No. 09/000,266, filed on Oct. 19, 1998.

(30) Foreign Application Priority Data

Jul. 19, 1995 (DE) .......................... 195 26 386
Jul. 19, 1996 (WO) .............................. PCT/DE96/01369

(51) Int. Cl.$^7$ .......................... C12P 21/06; C12N 15/00
(52) U.S. Cl. .................... 435/69.3; 435/69.1; 435/91.1; 435/91.33; 530/350; 530/403; 536/23.72
(58) Field of Search .............................. 435/69.3, 69.1, 435/91.1, 91.33; 530/350, 403; 536/23.72

(56) References Cited

FOREIGN PATENT DOCUMENTS

| DE | A44 15 743 | 11/1995 |
|---|---|---|
| EP | A0 301 289 | 2/1989 |
| EP | A0 370 625 | 5/1990 |
| WO | WOA94 05792 | 3/1994 |

OTHER PUBLICATIONS

Browne et al., 1988, "Analysis of the L1 Gene Product of Human Papillomavirus Type 16 by Expression in a Vaccinia Virus Recombinant," *J. Gen. Virology* 69: 1263–1273.

Egawa et al., 1993, "Two Novel Types of Human Papillomavirus, HPV 63 and HPV 65: Comparisons of their Clinical and Histological Features and DNA Sequences to Other HPV Types," *Virology* 194: 789–799.

Hagensee et al., 1993, "Self–Assembly of Human Papillomavirus Type 1 Capsids by Expression of the L1 Protein Alone or by Coexpression of the L1 and L2 Capsid Proteins," *Journal of Virology* 67: 315–322.

Jarrett et al., 1991, "Studies on Vaccination Against Papillomaviruses: Prophylactic and Therapeutic Vaccination with Recombinant Structural Protein," *Virology* 184:33–42.

Kirnbauer et al., 1993, "Efficient Self–Assembly of Human Papillomavirus Type 16 L1 and L1–L2 into Virus–Like Particles," *Journal of Virology* 67: 6929–6936.

Shamanin et al., 1994, "Specific Types of Human Papillomavirus Found in Benign Proliferations and Carcinomas of the Skin in Immunosuppressed Patients," *Cancer Research* 54: 4610–4613.

Shamanin et al., 1996, "Human Papillomavirus Infections in Nonmelanoma Skin Cancer from Renal Transplant Recipients and Nonimmunosuppressed Patients," *Journal of the National Cancer Institute* 88(12):802–811.

Syrjänen, K.J., 1980, "Bronchial Squamous Cell Carcinomas Associated with Epithelial Changes Identical to Condylomatous Lesions of the Uterine Cervix," *Lung* 158:131–142.

zur Hausen, H., 1976, "Biochemical Approaches to Detection of Epstein–Barr Virus in Human Tumors," *Cancer Research* 36: 678–680.

zur Hausen, H., 1976, "Condylomata Acuminata and Human Genital Cancer," *Cancer Research* 36:794.

zur Hausen, H., 1989, "Papillomaviruses in Anogenital Cancer as a Model to Understand the Role of Viruses in Human Cancers," *Cancer Research* 49: 4677–4681.

Xi et al., J. of Gen. Virology, 1991, vol. 72, pp. 2981–2988 (abstract only).

Zhou et al., Virology, 1991, vol. 185, pp. 251–257.

Tomita et al., J. of Virology, 1987, vol. 61, pp. 2389–2394.

Rose et al., J. of Virology, 1993, vol. 67, pp. 1936–1944.

*Primary Examiner*—Ali R. Salimi
(74) *Attorney, Agent, or Firm*—Pennie & Edmonds LLP

(57) ABSTRACT

This invention relates to a DNA coding for a peptide of a papilloma virus major capsid protein. Moreover, this invention deals with a papilloma virus genome containing such a DNA. Furthermore, this invention concerns proteins coded by the papilloma virus genome and virus-like particles as well as antibodies directed thereagainst and the use thereof for diagnosis, treatment and vaccination.

10 Claims, 10 Drawing Sheets vs19-6

```
      GGATCCATGCAGGATGGTGACATGTGTGATATAGGATTCGGAGCTTGCAATTTCAGGGCA
    1 ---------+---------+---------+---------+---------+---------+  60
      CCTAGGTACGTCCTACCACTGTACACACTATATCCTAAGCCTCGAACGTTAAAGTCCCGT a      G  S  M  Q  D  G  D  M  C  D  I  G  F  G  A  C  N  F  R  A    -

TTTCAGCAAGATAGGTCAGGTGTTCCTTTAGATATAGTAGATAGTACTTGCAAGTATCCA
   61 ---------+---------+---------+---------+---------+---------+ 120
      AAAGTCGTTCTATCCAGTCCACAAGGAAATCTATATCATCTATCATGAACGTTCATAGGT a      F  Q  Q  D  R  S  G  V  P  L  D  I  V  D  S  T  C  K  Y  P    -

GACTTTTTGAAAATGACAAAAGACAAGTATGGTGATGAATGCTTCTTTTTTGGTCGTCGA
  121 ---------+---------+---------+---------+---------+---------+ 180
      CTGAAAAACTTTTACTGTTTTCTGTTCATACCACTACTTACGAAGAAAAAACCAGCAGCT a      D  F  L  K  M  T  K  D  K  Y  G  D  E  C  F  F  F  G  R  R    -

GAGCAGTTGTATGCAAGGCATTATTTTACCAGAGCAGGCACAATAGGTGATTCTATTCCA
  181 ---------+---------+---------+---------+---------+---------+ 240
      CTCGTCAACATACGTTCCGTAATAAAATGGTCTCGTCCGTGTTATCCACTAAGATAAGGT a      E  Q  L  Y  A  R  H  Y  F  T  R  A  G  T  I  G  D  S  I  P    -

ACGCCATATCAGGAATCTGAATTTTACAGATCTCCACAGGATAGCCAGGCTCAGAATAAT
  241 ---------+---------+---------+---------+---------+---------+ 300
      TGCGGTATAGTCCTTAGACTTAAAATGTCTAGAGGTGTCCTATCGGTCCGAGTCTTATTA a      T  P  Y  Q  E  S  E  F  Y  R  S  P  Q  D  S  Q  A  Q  N  N    -

GTGGATTCTCACATTTATGTAGCCACTCCTAGTGGTTCTTTAACTAGCAGTGATGCTCAG
  301 ---------+---------+---------+---------+---------+---------+ 360
      CACCTAAGAGTGTAAATACATCGGTGAGGATCACCAAGAAATTGATCGTCACTACGAGTC a      V  D  S  H  I  Y  V  A  T  P  S  G  S  L  T  S  S  D  A  Q    -

CTGTTTAACAGACCTTATTGGCTCCAAAATGCTCAAGGTACCAATAACGGAATGGATCC
  361 ---------+---------+---------+---------+---------+--------- 419
      GACAAATTGTCTGGAATAACCGAGGTTTTACGAGTTCCATGGTTATTGCCTTACCTAGG a      L  F  N  R  P  Y  W  L  Q  N  A  Q  G  T  N  N  G  M  D      -
```

FIGURE 1 vs200-1

```
    GGATCCATGGAGGACGGTGAGATGGCAGACATAGGATATGGTAATCTTAATTTTAAAGCT
  1 ---------+---------+---------+---------+---------+---------+  60
    CCTAGGTACCTCCTGCCACTCTACCGTCTGTATCCTATACCATTAGAATTAAAATTTCGA a   G  S  M  E  D  G  E  M  A  D  I  G  Y  G  N  L  N  F  K  A   -

TTACAGGAAAATAGGCCTGATGTTAGTCTTGATATTGTCAATGAAACCTGCAAATATCCA
 61 ---------+---------+---------+---------+---------+---------+ 120
    AATGTCCTTTTATCCGGACTACAATCAGAACTATAACAGTTACTTTGGACGTTTATAGGT a   L  Q  E  N  R  P  D  V  S  L  D  I  V  N  E  T  C  K  Y  P   -

GATTTTTTGAAGATGCAAAATGATGTTTATGGAGACTCCTGTTTCTTTTTTGCTCGTAGA
121 ---------+---------+---------+---------+---------+---------+ 180
    CTAAAAAACTTCTACGTTTTACTACAAATACCTCTGAGGACAAAGAAAAAACGAGCATCT a   D  F  L  K  M  Q  N  D  V  Y  G  D  S  C  F  F  F  A  R  R   -

GAGCAATGTTATGCCAGACACTTTTTTGTAAGAGGTGGCAACGTAGGGGATGACATTCCT
181 ---------+---------+---------+---------+---------+---------+ 240
    CTCGTTACAATACGGTCTGTGAAAAAACATTCTCCACCGTTGCATCCCCTACTGTAAGGA a   E  Q  C  Y  A  R  H  F  F  V  R  G  G  N  V  G  D  D  I  P   -

GGTGAACAAATAGACGCAGGCACATATAAAAATGATTTTTACATTCCAGGAGCATCAGGT
241 ---------+---------+---------+---------+---------+---------+ 300
    CCACTTGTTTATCTGCGTCCGTGTATATTTTTACTAAAAATGTAAGGTCCTCGTAGTCCA a   G  E  Q  I  D  A  G  T  Y  K  N  D  F  Y  I  P  G  A  S  G   -

CAGACACAAAATAAAATAGGTAACTCCATGTATTTCCCAACAGTTAGTGGCTCATTAGTG
301 ---------+---------+---------+---------+---------+---------+ 360
    GTCTGTGTTTTATTTTATCCATTGAGGTACATAAAGGGTTGTCAATCACCGAGTAATCAC a   Q  T  Q  N  K  I  G  N  S  M  Y  F  P  T  V  S  G  S  L  V   -

TCTAGTGATGCTCAGCTGTTTAATAGGCCCTACTGGCTCCAACGCGCACAGGGCCACAAC
361 ---------+---------+---------+---------+---------+---------+ 420
    AGATCACTACGAGTCGACAAATTATCCGGGATGACCGAGGTTGCGCGTGTCCCGGTGTTG a   S  S  D  A  Q  L  F  N  R  P  Y  W  L  Q  R  A  Q  G  H  N   -

AACGGCGTGGATCC
421 ---------+---- 434
    TTGCCGCACCTAGG a   N  G  V  D     -
```

FIGURE 2 vs201-1

```
      GGATCCCTAGAGGATGGTGATATGGGTGATATAGGATTTGGGCATGCTAATTTTAGCCGT
    1 ---------+---------+---------+---------+---------+---------+ 60
      CCTAGGGATCTCCTACCACTATACCCACTATATCCTAAACCCGTACGATTAAAATCGGCA a       G  S  L  E  D  G  D  M  G  D  I  G  F  G  H  A  N  F  S  R   -

TTACAAGAAGATAAAGCAGGTGTGCCATTAGAATTAGTGGACACTTTTAGTATATGGCCT
   61 ---------+---------+---------+---------+---------+---------+ 120
      AATGTTCTTCTATTTCGTCCACACGGTAATCTTAATCACCTGTGAAAATCATATACCGGA a       L  Q  E  D  K  A  G  V  P  L  E  L  V  D  T  F  S  I  W  P   -

GACTTTTTACGCATGACCAGTGATATATATGGAGATGCTGTGTTTTTTTGGGGAAAGCGA
  121 ---------+---------+---------+---------+---------+---------+ 180
      CTGAAAAATGCGTACTGGTCACTATATATACCTCTACGACACAAAAAAACCCCTTTCGCT a       D  F  L  R  M  T  S  D  I  Y  G  D  A  V  F  F  W  G  K  R   -

GAACATATGTTTGCCAGACATTTATGGGCAAGAGCTGGAACTATGGGCGACGCTATTCCA
  181 ---------+---------+---------+---------+---------+---------+ 240
      CTTGTATACAAACGGTCTGTAAATACCCGTTCTCGACCTTGATACCCGCTGCGATAAGGT a       E  H  M  F  A  R  H  L  W  A  R  A  G  T  M  G  D  A  I  P   -

GATAATAATGCAGAGTTTTTTCTGCATCCCAATGGTGCACCTCAAAATAAGTTAGCCTCA
  241 ---------+---------+---------+---------+---------+---------+ 300
      CTATTATTACGTCTCAAAAAAGACGTAGGGTTACCACGTGGAGTTTTATTCAATCGGAGT a       D  N  N  A  E  F  F  L  H  P  N  G  A  P  Q  N  K  L  A  S   -

TTTGCTTATTTTCCAACACCTAGTGGTTCTCTTAATACCAGTGATAATCAATTGTTTAAT
  301 ---------+---------+---------+---------+---------+---------+ 360
      AAACGAATAAAAGGTTGTGGATCACCAAGAGAATTATGGTCACTATTAGTTAACAAATTA a       F  A  Y  F  P  T  P  S  G  S  L  N  T  S  D  N  Q  L  F  N   -

AAGCCGTATTGGTTGCGAAAAGCTCAGGGCACCAACAATGGGATGGATCC
  361 ---------+---------+---------+---------+------+ 410
      TTCGGCATAACCAACGCTTTTCGAGTCCCGTGGTTGTTACCCTACCTAGG a       K  P  Y  W  L  R  K  A  Q  G  T  N  N  G  M  D   -
```

FIGURE 3 vs202-8

```
       GGATCCATTGAGGATGCGGATATGAGTGATATAGGATTTGGAGCTGTGAATTTTAGCACT
    1  ---------+---------+---------+---------+---------+---------+ 60
       CCTAGGTAACTCCTACGCCTATACTCACTATATCCTAAACCTCGACACTTAAAATCGTGA a      G  S  I  E  D  A  D  M  S  D  I  G  F  G  A  V  N  F  S  T  -

TTCTCTGAAAGCCGGGCTGATGCACCTTTAGAATTAATCAATTCTATTAGTAAATGGCCT
   61  ---------+---------+---------+---------+---------+---------+ 120
       AAGAGACTTTCGGCCCGACTACGTGGAAATCTTAATTAGTTAAGATAATCATTTACCGGA a      F  S  E  S  R  A  D  A  P  L  E  L  I  N  S  I  S  K  W  P  -

GATTTTATTCAAATGTCTAAGGATATTTATGGCGATAGAATGTTTTTCTTTGGAAAACGT
  121  ---------+---------+---------+---------+---------+---------+ 180
       CTAAAATAAGTTTACAGATTCCTATAAATACCGCTATCTTACAAAAAGAAACCTTTTGCA a      D  F  I  Q  M  S  K  D  I  Y  G  D  R  M  F  F  F  G  K  R  -

GAGCAGATGTATGCAAGACACACATTTTGTAAAGATGGTGCTGTGGGAGATGCTATTCCA
  181  ---------+---------+---------+---------+---------+---------+ 240
       CTCGTCTACATACGTTCTGTGTGTAAAACATTTCTACCACGACACCCTCTACGATAAGGT a      E  Q  M  Y  A  R  H  T  F  C  K  D  G  A  V  G  D  A  I  P  -

GAAAATTTAAATAATGATGAGGATGTTCATCATAGGTTTTTATTAAATCCTAAGCCTGAC
  241  ---------+---------+---------+---------+---------+---------+ 300
       CTTTTAAATTTATTACTACTCCTACAAGTAGTATCCAAAAATAATTTAGGATTCGGACTG a      E  N  L  N  N  D  E  D  V  H  H  R  F  L  L  N  P  K  P  D  -

GCACCACCATATTCAAACTTAGGAAACAGTACTTACTTTCCTATGCCAAGTGGTTCATTA
  301  ---------+---------+---------+---------+---------+---------+ 360
       CGTGGTGGTATAAGTTTGAATCCTTTGTCATGAATGAAAGGATACGGTTCACCAAGTAAT a      A  P  P  Y  S  N  L  G  N  S  T  Y  F  P  M  P  S  G  S  L  -

GTTAGTAGTGAAACTCAATTATTTAACAGACCATTTTGGCTACATCGAGCACAGGGCACC
  361  ---------+---------+---------+---------+---------+---------+ 420
       CAATCATCACTTTGAGTTAATAAATTGTCTGGTAAAACCGATGTAGCTCGTGTCCCGTGG a      V  S  S  E  T  Q  L  F  N  R  P  F  W  L  H  R  A  Q  G  T  -

AATAACGGCATGGATCC
  421  ---------+------- 437
       TTATTGCCGTACCTAGG a      N  N  G  M  D  -
```

FIGURE 4 vs203-2

```
        GGATCCATGGAGGATGGTGAAATGGGCGACATAGGCTTTGGAGCCTTTAATTTTAAAGCC
      1 ------------------------------------------------------------  60
        CCTAGGTACCTCCTACCACTTTACCCGCTGTATCCGAAACCTCGGAAATTAAAATTTCGG a       G  S  M  E  D  G  E  M  G  D  I  G  F  G  A  F  N  F  K  A   -

CTACAGAAAGATCGTGCTGGTGTTAGTTTAGATTTAGTTGATACATTCAGTATATGGCCA
     61 ------------------------------------------------------------ 120
        GATGTCTTTCTAGCACGACCACAATCAAATCTAAATCAACTATGTAAGTCATATACCGGT a       L  Q  K  D  R  A  G  V  S  L  D  L  V  D  T  F  S  I  W  P   -

GACTTTTTAAAAATGACTAATGATATATATGGTGACAGTATCTTTTTTTATGGTAAAAGA
    121 ------------------------------------------------------------ 180
        CTGAAAAATTTTTACTGATTACTATATATACCACTGTCATAGAAAAAAATACCATTTTCT a       D  F  L  K  M  T  N  D  I  Y  G  D  S  I  F  F  Y  G  K  R   -

GAACAGCTATTTAGTAGACACTTGTGGGCCCGCGCAGGAACGGCTGGAGATGCCATTCCA
    181 ------------------------------------------------------------ 240
        CTTGTCGATAAATCATCTGTGAACACCCGGGCGCGTCCTTGCCGACCTCTACGGTAAGGT a       E  Q  L  F  S  R  H  L  W  A  R  A  G  T  A  G  D  A  I  P   -

TCTCCTGATAACAAAAATCTAATATTTCAGGGTGATGATGCAGTGCCACAAAAGACTGCT
    241 ------------------------------------------------------------ 300
        AGAGGACTATTGTTTTTAGATTATAAAGTCCCACTACTACGTCACGGTGTTTTCTGACGA a       S  P  D  N  K  N  L  I  F  Q  G  D  D  A  V  P  Q  K  T  A   -

GGGTCTTTTACTTATTTTAGTGCCCCTAGTGGGTCATTAACAACTAGTGATTCTCAGTTA
    301 ------------------------------------------------------------ 360
        CCCAGAAAATGAATAAAATCACGGGGATCACCCAGTAATTGTTGATCACTAAGAGTCAAT a       G  S  F  T  Y  F  S  A  P  S  G  S  L  T  T  S  D  S  Q  L   -

TTTAATAGGCCATATTGGTTAAGAAGAGCTCAAGGTACCAACAACGGTGTGGATCC
    361 -------------------------------------------------------      416
        AAATTATCCGGTATAACCAATTCTTCTCGAGTTCCATGGTTGTTGCCACACCTAGG a       F  N  R  P  Y  W  L  R  R  A  Q  G  T  N  N  G  V  D         -
```

FIGURE 5 vs204-4

```
    GGATCCATGGAGGACGGTGAGATGAGTGATACAGGTTTTGGTGCTATGAATTTTGATAAT
  1 ---------+---------+---------+---------+---------+---------+ 60
    CCTAGGTACCTCCTGCCACTCTACTCACTATGTCCAAAACCACGATACTTAAAACTATTA a    G  S  M  E  D  G  E  M  S  D  T  G  F  G  A  M  N  F  D  N   -

CTATGCGAGGACAGAGCTTCATTTCCTTTAGACATTATAAATGAGACCTCCAAGTGGCCT
 61 ---------+---------+---------+---------+---------+---------+ 120
    GATACGCTCCTGTCTCGAAGTAAAGGAAATCTGTAATATTTACTCTGGAGGTTCACCGGA a    L  C  E  D  R  A  S  F  P  L  D  I  I  N  E  T  S  K  W  P   -

GATTTTCTAAAAATGAATAAAGATCCTTATGGAGATCATATATTTTTCTTTGGTTTACGA
121 ---------+---------+---------+---------+---------+---------+ 180
    CTAAAAGATTTTTACTTATTTCTAGGAATACCTCTAGTATATAAAAAGAAACCAAATGCT a    D  F  L  K  M  N  K  D  P  Y  G  D  H  I  F  F  F  G  L  R   -

GAGCAGTTATATTCCAGACATCATGGTGCTCGGGGAGGAAAAATGGGAGATACTATTCCA
181 ---------+---------+---------+---------+---------+---------+ 240
    CTCGTCAATATAAGGTCTGTAGTACCACGAGCCCCTCCTTTTTACCCTCTATGATAAGGT a    E  Q  L  Y  S  R  H  H  G  A  R  G  G  K  M  G  D  T  I  P   -

GAAAATACAGCAGGCGAATATTATTATCCTCCTACTGATGGTGCTCAGCAAAATATAGGT
241 ---------+---------+---------+---------+---------+---------+ 300
    CTTTTATGTCGTCCGCTTATAATAATAGGAGGATGACTACCACGAGTCGTTTTATATCCA a    E  N  T  A  G  E  Y  Y  Y  P  P  T  D  G  A  Q  Q  N  I  G   -

TCACATATTTATTTCAATACTGTTAGTGGATCTTTAACATCTTCAGAAACTCAGATATTT
301 ---------+---------+---------+---------+---------+---------+ 360
    AGTGTATAAATAAAGTTATGACAATCACCTAGAAATTGTAGAAGTCTTTGAGTCTATAAA a    S  H  I  Y  F  N  T  V  S  G  S  L  T  S  S  E  T  Q  I  F   -

AATAGGCCATATTTTTTACAACGTGCACAGGGCACAAACAACGGAGTGGATCC
361 ---------+---------+---------+---------+---------+---  413
    TTATCCGGTATAAAAAATGTTGCACGTGTCCCGTGTTTGTTGCCTCACCTAGG a    N  R  P  Y  F  L  Q  R  A  Q  G  T  N  N  G  V  D      -
```

FIGURE 6 vs205-1

```
     GGATCCATTCAAGATGGGGATATGTGCGATATTGGCTTTGGAGCAGCCAATTTTAAAGCA
   1 ---------+---------+---------+---------+---------+---------+  60
     CCTAGGTAAGTTCTACCCCTATACACGCTATAACCGAAACCTCGTCGGTTAAAATTTCGT
``` a    G  S  I  Q  D  G  D  M  C  D  I  G  F  G  A  A  N  F  K  A  -

```
     TTACAGCAAGATAAATCAGGTGTTCCTTTAGATATTGTTGACAGTATATGTAAATGGCCA
  61 ---------+---------+---------+---------+---------+---------+ 120
     AATGTCGTTCTATTTAGTCCACAAGGAAATCTATAACAACTGTCATATACATTTACCGGT
``` a    L  Q  Q  D  K  S  G  V  P  L  D  I  V  D  S  I  C  K  W  P  -

```
     GATATTATTAAAATGGAGCAAGAAATATATGGAGACAGATTATTTTTCTTTACTAAACGT
 121 ---------+---------+---------+---------+---------+---------+ 180
     CTATAATAATTTTACCTCGTTCTTTATATACCTCTGTCTAATAAAAGAAATGATTTGCA
``` a    D  I  I  K  M  E  Q  E  I  Y  G  D  R  L  F  F  F  T  K  R  -

```
     GAGCAAGCTTATGCCAGGCATTATTTCGCTCGTGCAGGAATTAATGGTGATTCTTTACCA
 181 ---------+---------+---------+---------+---------+---------+ 240
     CTCGTTCGAATACGGTCCGTAATAAAGCGAGCACGTCCTTAATTACCACTAAGAAATGGT
``` a    E  Q  A  Y  A  R  H  Y  F  A  R  A  G  I  N  G  D  S  L  P  -

```
     GATGCAATGAAACCAGGAGAATATTATCTCTCTCCTAAGTTGGGAGATGAGCAAGTACCC
 241 ---------+---------+---------+---------+---------+---------+ 300
     CTACGTTACTTTGGTCCTCTTATAATAGAGAGAGGATTCAACCCTCTACTCGTTCATGGG
``` a    D  A  M  K  P  G  E  Y  Y  L  S  P  K  L  G  D  E  Q  V  P  -

```
     CAGAAAGACTTAGGATCGCATATTTATTTTCCTACAGTTAGTGGTTCTTTGGTTTCTAGT
 301 ---------+---------+---------+---------+---------+---------+ 360
     GTCTTTCTGAATCCTAGCGTATAAATAAAAGGATGTCAATCACCAAGAAACCAAAGATCA
``` a    Q  K  D  L  G  S  H  I  Y  F  P  T  V  S  G  S  L  V  S  S  -

```
     GAAAATCAGTTATTTAACAGACCATATTGGTTGCAGAAATCTCAGGGCACAAACAACGGC
 361 ---------+---------+---------+---------+---------+---------+ 420
     CTTTTAGTCAATAAATTGTCTGGTATAACCAACGTCTTTAGAGTCCCGTGTTTGTTGCCG
``` a    E  N  Q  L  F  N  R  P  Y  W  L  Q  K  S  Q  G  T  N  N  G  -

```
     GTGGATCC
 421 -------- 428
     CACCTAGG
``` a    V  D  -

FIGURE 7 vs206-2

```
      GGATCCCTGGAAGATGGTGAAATGGGAGATATTGGGTTTGGTGCAGCAAATTTTAAAACG
   1  ---------+---------+---------+---------+---------+---------+  60
      CCTAGGGACCTTCTACCACTTTACCCTCTATAACCCAAACCACGTCGTTTAAAATTTTGC a      G  S  L  E  D  G  E  M  G  D  I  G  F  G  A  A  N  F  K  T   -

TTACAAAAGGACAGAGCCGGAGTCAGCTTAGATTTAGTAGACACTTTTAGCATTTGGCCT
  61  ---------+---------+---------+---------+---------+---------+ 120
      AATGTTTTCCTGTCTCGGCCTCAGTCGAATCTAAATCATCTGTGAAAATCGTAAACCGGA a      L  Q  K  D  R  A  G  V  S  L  D  L  V  D  T  F  S  I  W  P   -

GACTTTTTAAAAATGACTAATGATATTTACGGAGATAGTATGTTTTTCTTTGGAAAACGT
 121  ---------+---------+---------+---------+---------+---------+ 180
      CTGAAAAATTTTTACTGATTACTATAAATGCCTCTATCATACAAAAGAAACCTTTTGCA a      D  F  L  K  M  T  N  D  I  Y  G  D  S  M  F  F  F  G  K  R   -

GAGCAGCTCTTTGGCAGACATCTTTGGACAAGAGCAGGTACTCCCGGCGATGCAATTCCT
 181  ---------+---------+---------+---------+---------+---------+ 240
      CTCGTCGAGAAACCGTCTGTAGAAACCTGTTCTCGTCCATGAGGGCCGCTACGTTAAGGA a      E  Q  L  F  G  R  H  L  W  T  R  A  G  T  P  G  D  A  I  P   -

ACTCCAGAAAATATAAACTTAATATTTCCAGCTGATGATGGCACTAGTCAAAAGGATGCA
 241  ---------+---------+---------+---------+---------+---------+ 300
      TGAGGTCTTTTATATTTGAATTATAAAGGTCGACTACTACCGTGATCAGTTTTCCTACGT a      T  P  E  N  I  N  L  I  F  P  A  D  D  G  T  S  Q  K  D  A   -

GGGTCTTTCACTTACTTTACTTCAGCTAGTGGATCTCTTAATACTAGCGATTCACAATTA
 301  ---------+---------+---------+---------+---------+---------+ 360
      CCCAGAAAGTGAATGAAATGAAGTCGATCACCTAGAGAATTATGATCGCTAAGTGTTAAT a      G  S  F  T  Y  F  T  S  A  S  G  S  L  N  T  S  D  S  Q  L   -

TTTAATAGACCTTACTGGCTTCGACGTGCACAAGGCACAAACAATGGCGTGGATCC
 361  ---------+---------+---------+---------+---------+------ 416
      AAATTATCTGGAATGACCGAAGCTGCACGTGTTCCGTGTTTGTTACCGCACCTAGG a      F  N  R  P  Y  W  L  R  R  A  Q  G  T  N  N  G  V  D    -
```

FIGURE 8 vs207-22

```
        GGATCCCTAGAGGATGGGGAGATGGGTGATATAGGATTTGGTGCTGCTAATTTTGCTAAG
      1 ---------+---------+---------+---------+---------+---------+ 60
        CCTAGGGATCTCCTACCCCTCTACCCACTATATCCTAAACCACGACGATTAAAACGATTC a        G  S  L  E  D  G  E  M  G  D  I  G  F  G  A  A  N  F  A  K   -

CTTATGCAAGATAGAGCTGGTGTACCTCTGGAATTAATAGATAGTATTAGTATATGGCCA
     61 ---------+---------+---------+---------+---------+---------+ 120
        GAATACGTTCTATCTCGACCACATGGAGACCTTAATTATCTATCATAATCATATACCGGT a        L  M  Q  D  R  A  G  V  P  L  E  L  I  D  S  I  S  I  W  P   -

GATTTTCTAAAAATGACAAAGGATATTTATGGAAATGAAGTATTTTTCTTTGGAAAACGC
    121 ---------+---------+---------+---------+---------+---------+ 180
        CTAAAAGATTTTTACTGTTTCCTATAAATACCTTTACTTCATAAAAAGAAACCTTTTGCG a        D  F  L  K  M  T  K  D  I  Y  G  N  E  V  F  F  F  G  K  R   -

GAGCAATGTTATGCTCGCCATTTATTTGCCAGAGCTGGTACTATGGGAGAACCAGTACCT
    181 ---------+---------+---------+---------+---------+---------+ 240
        CTCGTTACAATACGAGCGGTAAATAAACGGTCTCGACCATGATACCCTCTTGGTCATGGA a        E  Q  C  Y  A  R  H  L  F  A  R  A  G  T  M  G  E  P  V  P   -

AATGAGACTAATGGAGTAAATTTTATAAATGCAAAACCAGGAGATCCAAATCCCAGGAGC
    241 ---------+---------+---------+---------+---------+---------+ 300
        TTACTCTGATTACCTCATTTAAAATATTTACGTTTTGGTCCTCTAGGTTTAGGGTCCTCG a        N  E  T  N  G  V  N  F  I  N  A  K  P  G  D  P  N  P  R  S   -

GCTCATATGGGTTCTTCAGTATACTTTGCAACACCTAGTGGCTCCCTTAATACCAGTGAT
    301 ---------+---------+---------+---------+---------+---------+ 360
        CGAGTATACCCAAGAAGTCATATGAAACGTTGTGGATCACCGAGGGAATTATGGTCACTA a        A  H  M  G  S  S  V  Y  F  A  T  P  S  G  S  L  N  T  S  D   -

TCACAAATATTTAACAGACCTTATTGGTTACGACGGGCTCAAGGAACGAACAACGGCATG
    361 ---------+---------+---------+---------+---------+---------+ 420
        AGTGTTTATAAATTGTCTGGAATAACCAATGCTGCCCGAGTTCCTTGCTTGTTGCCGTAC a        S  Q  I  F  N  R  P  Y  W  L  R  R  A  Q  G  T  N  N  G  M   -

GATCC
    421 ----- 425
        CTAGG a        D   -
```

FIGURE 9 vs208-1

```
     GGATCCCTTGAGGATGGGGAAATGATAGATACAGGCTATGGTGCCATGGACTTTCGTACA
  1  ---------+---------+---------+---------+---------+---------+  60
     CCTAGGGAACTCCTACCCCTTTACTATCTATGTCCGATACCACGGTACCTGAAAGCATGT a    G  S  L  E  D  G  E  M  I  D  T  G  Y  G  A  M  D  F  R  T    -

TTGCAGGAAACCAAAAGTGAGGTACCACTAGATATTTGCCAATCCGTGTGTAAATATCCT
 61  ---------+---------+---------+---------+---------+---------+  120
     AACGTCCTTTGGTTTTCACTCCATGGTGATCTATAAACGGTTAGGCACACATTTATAGGA a    L  Q  E  T  K  S  E  V  P  L  D  I  C  Q  S  V  C  K  Y  P    -

GATTATTTGCAGATGTCTGCTGATGTATATGGGGACAGTATGTTTTTTTGTTTGCGCAAG
121  ---------+---------+---------+---------+---------+---------+  180
     CTAATAAACGTCTACAGACGACTACATATACCCCTGTCATACAAAAAAACAAACGCGTTC a    D  Y  L  Q  M  S  A  D  V  Y  G  D  S  M  F  F  C  L  R  K    -

GAACAGTTGTTTGCCAGGCACTTTTGGAATAGAGGTGGCATGGTGGGCGACACAATACCT
181  ---------+---------+---------+---------+---------+---------+  240
     CTTGTCAACAAACGGTCCGTGAAAACCTTATCTCCACCGTACCACCCGCTGTGTTATGGA a    E  Q  L  F  A  R  H  F  W  N  R  G  G  M  V  G  D  T  I  P    -

TCAGAGTTATATATTAAAGGCACGGATATACGTGAGCGTCCTGGTACTCATGTATATTCC
241  ---------+---------+---------+---------+---------+---------+  300
     AGTCTCAATATATAATTTCCGTGCCTATATGCACTCGCAGGACCATGAGTACATATAAGG a    S  E  L  Y  I  K  G  T  D  I  R  E  R  P  G  T  H  V  Y  S    -

CCTTCCCCAAGTGGCTCTATGGTCTCTTCTGATTCCCAGTTGTTTAATAAGCCCTATTGG
301  ---------+---------+---------+---------+---------+---------+  360
     GGAAGGGGTTCACCGAGATACCAGAGAAGACTAAGGGTCAACAAATTATTCGGGATAACC a    P  S  P  S  G  S  M  V  S  S  D  S  Q  L  F  N  K  P  Y  W    -

TTGCATAAGGCCCAAGGCCACAATAACGGGATGGATCC
361  ---------+---------+---------+-------- 398
     AACGTATTCCGGGTTCCGGTGTTATTGCCCTACCTAGG a    L  H  K  A  Q  G  H  N  N  G  M  D     -
```

PAPILLOMA VIRUSES, AGENTS FOR DETECTING THEM AND FOR TREATING DISEASES CAUSED BY SUCH VIRUSES

This is a division, of application Ser. No. 09/000,266 filed Oct. 19, 1998.

TABLE OF CONTENTS
I. FIELD OF THE INVENTION
II. BACKGROUND OF THE INVENTION
III. SUMMARY OF THE INVENTION
IV. BRIEF DESCRIPTION OF THE DRAWINGS
V. DETAILED DESCRIPTION OF THE INVENTION
VI. EXAMPLES
   A. Example 1: Identification of the Papilloma Virus Genome VS19-6-G
   B. Example 2: Cloning of the Papilloma Virus Genome VS19-6-G
WHAT IS CLAIMED:
ABSTRACT This is a national phase filing of the application Ser. No. PCT/DE96/01369, which was filed with the Patent Corporation Treaty on Jul. 19, 1996, and is entitled to priority of the German Patent Application P 195 26 386.3, filed Jul. 19, 1995.

I. FIELD OF THE INTENTION

This invention relates to a DNA coding for a peptide of a papilloma virus major capsid protein. Moreover, this invention deals with a papilloma virus genome containing such a DNA. In addition, this invention concerns proteins coded by the papilloma virus genome and virus-like particles as well as antibodies directed against them and their use for diagnosis, treatment and vaccination.

II. BACKGROUND OF THE INVENTION

It is known that papilloma viruses infect the epithelium of human beings and animals. Human papilloma viruses (hereinafter referred to as HP viruses) are found in benign epithelial neoplasms, e.g. warts, condylomas in the genital zone, and malignant epithelial neoplasms, e.g. carcinomas of the skin and the uterus. Zur Hausen, 1989, *Cancer Research* 49:4677–4681. HP viruses are also considered for the growth of malignant tumors in the respiratory tract. Zur Hausen, 1976, *Cancer Research* 36:530. Besides, HP viruses are considered at least jointly responsible for the growth of squamous carcinomas of the lung. Syrjanen, 1980, *Lung* 158:131–142.

Papilloma viruses have an icosahedral capsid without envelope in which a circular, double-stranded DNA molecule of about 7900 bp is present. The capsid comprises a major capsid protein (L1) and a minor capsid protein (L2). Both proteins, coexpressed or L1 expressed alone, result in vitro in the formation of virus-like particles Kimbauer et al., 1993, *Journal of Virology* 67:6929–6936.

Papilloma viruses cannot be proliferated in monolayer cell culture. Therefore, their characterization is extremely difficult, the detection of papilloma viruses already creating considerable problems. This applies especially to papilloma viruses in carcinomas of the skin. A reliable detection thereof and thus well-calculated steps taken thereagainst are not possible by now.

Thus, it is the object of the present invention to provide a product by which papilloma viruses can be detected, particularly in carcinomas of the skin. Furthermore, a product should be provided to be able to take therapeutic steps against these papilloma viruses.

III. SUMMARY OF THIS INVENTION

This invention relates to a DNA coding for a peptide of a papilloma virus major capsid protein. Moreover, this invention deals with a papilloma virus genome containing such a DNA. Furthermore, this invention concerns proteins coded by the papilloma virus genome and virus-like particles as well as antibodies directed thereagainst and the use thereof for diagnosis, treatment and vaccination.

IV. BRIEF DESCRIPTION OF THE DRAWINGS

FIG. 1 shows the base sequence and the amino acid sequence, derived therefrom, of a DNA coding for a peptide of L1 of a papilloma virus. This DNA was deposited as plasmid VS19-6 with DSM (*Deutsche Sammlung von Mikroorganismen und Zellkulturen*[German-type collection of micro-organisms and cell cultures]) under DSM 10104 on Jul. 11, 1995.

FIG. 2 shows the base sequence and the amino acid sequence, derived therefrom, of a DNA coding for a peptide of L1 of a papilloma virus. This DNA was deposited as plasmid VS200-1 with DSM under DSM 10096 on Jul. 11, 1995.

FIG. 3 shows the base sequence and the amino acid sequence, derived therefrom, of a DNA coding for a peptide of L1 of a papilloma virus. This DNA was deposited as plasmid VS201-1 with DSM under DSM 10097 on Jul. 11, 1995.

FIG. 4 shows the base sequence and the amino acid sequence, derived therefrom, of a DNA coding for a peptide of L1 of a papilloma virus. This DNA was deposited as plasmid VS202-8 with DSM under DSM 10098 on Jul. 11, 1995.

FIG. 5 shows the base sequence and the amino acid sequence, derived therefrom, of a DNA coding for a peptide of L1 of a papilloma virus. This DNA was deposited as plasmid VS203-2 with DSM under DSM 10099 on Jul. 11, 1995.

FIG. 6 shows the base sequence and the amino acid sequence, derived therefrom, of a DNA coding for a peptide of L1 of a papilloma virus. This DNA was deposited as plasmid VS204-4 with DSM under DSM 10100 on Jul. 11, 1995.

FIG. 7 shows the base sequence and the amino acid sequence, derived therefrom, of a DNA coding for a peptide of L1 of a papilloma virus. This DNA was deposited as plasmid VS205-1 with DSM under DSM 10101 on Jul. 11, 1995.

FIG. 8 shows the base sequence and the amino acid sequence, derived therefrom, of a DNA coding for a peptide of L1 of a papilloma virus. This DNA was deposited as plasmid VS206-2 with DSM under DSM 10109 on Jul. 13, 1995.

FIG. 9 shows the base sequence and the amino acid sequence, derived therefrom, of a DNA coding for a peptide of L1 of a papilloma virus. This DNA was deposited as plasmid VS207-22 with DSM under DSM 10102 on Jul. 11, 1995.

FIG. 10 shows the base sequence and the amino acid sequence, derived therefrom, of a DNA coding for a peptide of L1 of a papilloma virus. This DNA was deposited as plasmid VS208-1 with DSM under DSM 10103 on Jul. 11, 1995.

V. DETAILED DESCRIPTION OF THE INVENTION

It is the object of the present invention to provide a product by which papilloma viruses can be detected, particularly in carcinomas of the skin. Furthermore, a product is provided which enables to take therapeutic steps against these papilloma viruses.

Accordingly, the subject matter of the invention relates to a DNA coding for a peptide of a papilloma virus major capsid protein (L1), the peptide comprising the amino acid sequence of FIG. 1, FIG. 2, FIG. 3, FIG. 4, FIG. 5, FIG. 6, FIG. 7, FIG. 8, FIG. 9 or FIG. 10 or an amino acid sequence differing therefrom by one or more amino acids.

A further subject matter of the invention relates to a DNA coding for a peptide of a papilloma virus major capsid protein, the DNA comprising the base sequence of FIG. 1, FIG. 2, FIG. 3, FIG. 4, FIG. 5, FIG. 6, FIG. 7, FIG. 8, FIG. 9 or FIG. 10 or a base sequence differing therefrom by one or more base pairs.

The above DNA has the following sequence homology with respect to known papilloma viruses:

| | |
|---|---|
| DNA of FIG. 1: | 69.1% with respect to HP virus 65 |
| DNA of FIG. 2: | 80.7% with respect to HP virus 24 |
| DNA of FIG. 3: | 69.4% with respect to HP virus 48 |
| DNA of FIG. 4: | 66.3% with respect to HP virus 48 |
| DNA of FIG. 5: | 66.9% with respect to HP virus 65 |
| DNA of FIG. 6: | 66.4% with respect to HP virus 65 |
| DNA of FIG. 7: | 69.1% with respect to HP virus 4 |
| DNA of FIG. 8: | 68.7% with respect to HP virus 48 |
| DNA of FIG. 9: | 76.6% with respect to HP virus 48 |
| DNA of FIG. 10: | 81.8% with respect to HP virus 68 |

According to the invention, the above DNA can be present in a vector and expression vector, respectively. A person skilled in the art is familiar with examples thereof. In the case of an expression vector for *E. coli*, these are e.g. pGEMEX, pUC derivatives, pGEM-T and pGEX-2T. For the expression in yeast e.g. pY100 and Ycpad1 have to be mentioned, while for the expression in animal cells e.g. pKCR, pEF-BOS, cDM8 and pCEV4 have to be indicated.

The person skilled in the art knows suitable cells to express the above DNA present in an expression vector. Examples of such cells comprise the *E. coli* strains HB101, DH1, x1776, JM101, JM 109, and XL1-Blue, the yeast strain *Saccharomyces cerevisiae* and the animal cells L, NH-3T3, FM3A, CHO, COS, Vero, and HeLa.

The person skilled in the art knows in which way the above DNA has to be inserted in an expression vector. He is also familiar with the fact that the above DNA can be inserted in connection with a DNA coding for another protein and peptide, respectively, so that the above DNA can be expressed in the form of a fusion protein.

A further subject matter of the invention relates to a papilloma virus genome which comprises the above DNA. The expression "papilloma virus genome" also comprises an incomplete genome, i.e. fragments of a papilloma virus genome, which comprise the above DNA. This may be e.g. a DNA coding for L1 or a portion thereof.

A common process can be used for the provision of the above papilloma virus genome, which comprises the following processing steps:

(a) isolation of the total DNA from a biopsy of epithelial neoplasm,
(b) hybridization of the total DNA of (a) with the above DNA so as to detect a papilloma virus genome included in the total DNA of (a), and
(c) cloning of the total DNA of (a) containing the papilloma virus genome, in a vector and optionally subdloning the resulting clone, all processing steps originating from common DNA recombination technique.

As far as the isolation, hybridization and cloning of cell DNA is concerned, reference is made by way of supplement to Sambrook et al., *Molecular Cloning A Laboratory Manual*, second edition, Cold Spring Harbor Laboratory (1989).

The expression "epithelial neoplasm" comprises any neoplasms of epithelium in man and animal. Examples of such neoplasms are warts, condylomas in the genital zone and carcinomas of the skin. The latter are used preferably to isolate the above papilloma virus genome.

The expression "vector" comprises any vectors suitable for cloning chromosomal DNA and extrachromosomal DNA, respectively. Examples of such vectors are cosmids such as pWE15 and Super Cos1, and phages such as λ-phages, e.g. λZAP expression vector, λZAPII vector and λgt10 vector. In the present case, λ-phages are used preferably. The above vectors are known and obtainable from the company of Stratagene.

Papilloma virus genomes according to the invention may be present in integrated form in chromosomal DNA or in extrachromosomal fashion. The person skilled in the art is familiar with processes serving the clarification thereof. He also knows processes serving for finding out the optimum restriction enzymes for cloning the papilloma virus genomes. He will orient himself by genomes of known papilloma viruses. In particular, the person skilled in the art will pay corresponding attention to the above-mentioned HP viruses.

The provision of a papilloma virus genome referred to as VS 19-6 is described by way of example. For this purpose, the total DNA is isolated from a biopsy of a squamous cell carcinoma, cleaved by BamHI and separated eletrophoretically in an agarose gel. The agarose gel is then subjected to a blotting method so as to transfer the DNA to a nitrocellulose membrane. It is inserted in a hybridization method in which the DNA of FIG. 1 is used as labeled sample, optionally in combination with a DNA of HP virus 65. Hybridization with the papilloma virus DNA present in the total DNA is obtained.

Moreover, the above total DNA cleaved by BamHI is cloned in a λ-phage. The corresponding clones, i.e. the clones containing the papilloma virus DNA are identified by hybridization with the DNA of FIG. 1, optionally in combination with a DNA of the HP virus 65. The insert of these clones is then subjected to a further cloning in a plasmid vector so as to obtain a clone which contains the papilloma virus genome VS19-6-G. The genome is confirmed by sequencing.

Further papilloma virus genomes are provided analogously. They are designated in accordance with the DNAs used for their provision, namely by: VS200-1-G, VS201-1-G, VS202-8-G, VS203-2-G, V8204-4-G, VS205-1-G, VS206-2-G, VS and VS208-1-G, respectively.

A further subject matter of the invention relates to a protein which is coded by the above papilloma virus genome. Such a protein is e.g. a major capsid protein (L1) or a minor capsid protein (L2). An above protein is prepared as usual. The preparation of L1 and L2, respectively, of the papilloma virus genome VS19-6-G is described by way of example. For this purpose, the HP virus 65 related to the DNA of FIG. 1 is used. The fill sequence and the position of individual DNA regions coding for proteins are known in connection therewith. These DNAs are identified on the papilloma virus genome VS19-6-G by parallel restriction cleavages of both genomes and subsequent hybridization with various fragments concerning the DNA encoding L1 and L2, respectively. They are confirmed by sequencing. The DNA coding for L1 is referred to as VS19-6-G-L1 DNA and the DNA coding for L2 is referred to as VS19-6-G-L2 DNA.

Furthermore, the DNA coding for L1 and L2, respectively, is inserted in an expression vector. Examples thereof are mentioned above for *E. coli*, yeast and animal cells. In this connection, reference is made to the vector pGEX-2T as regards the expression in *E. coli* by way of supplement. Kirnbauer et al., supra. Having inserted the VS19-6-G-L1 DNA and VS19-6-G-L2 DNA, one obtains pGEX-2T-VS19-6-G-L1 and pGEX-2T-VS19-6-G-L2, respectively. After transforming *E. coli*, these expression vectors express a glutathione S transferase L1 fusion protein and glutathione S transferase L2 fusion protein, respectively. The proteins are purified as usual.

The bacculovirus system and vaccinia virus system, respectively, is mentioned for a further expression of the above DNA encoding L1 and L2, respectively. Expression vectors usable for this purpose are e.g. pEV mod. and pSynwtVI⁻ for the bacculovirus system. Kirnbauer et al., supra. Especially vectors with the vaccinia virus "early" (p7.5k) promoter and "late" (Psynth, p11K) promoter, respectively, have to be mentioned for the vaccinia virus system. Hagensee et al., 1993, *Journal of Virology* 67:315–322. The bacculovirus system is preferred in the present case. Having inserted the above DNA encoding L1 and L2, respectively, in pEV mod., one obtains pEVmod.-VS19-6-G-L1 and pEVmod.-VS19-6-G-L2, respectively.

The former expression vector as such or both expression vectors jointly lead to the formation of virus-like particles after infection of SF-9 insect cells. In the former case, such a particle comprises an L1 protein, while in the latter case, it contains an L2 protein in addition to an L1 protein.

A virus-like particle of the latter case is also obtained by inserting the above VS19-6-G-L1 and VS19-6-G-L2 DNAs jointly in the expression vector pSynwtVI⁻ and using the resulting pSynwtVI⁻VS19-6-G-L1/L2 for the infection of SF-9 insect cells. The above virus-like particles are purified as usual. They also represent a subject matter of the invention.

A further subject matter of the invention relates to an antibody directed against an above protein and virus-like particle, respectively. The preparation thereof is made as usual. It is described by way of example for the preparation of an antibody which is directed against a virus-like particle comprising L1 of VS19-6-G. For this purpose, the virus-like particle is injected subcutaneously into BALB/c mice. This injection is repeated at intervals of 3 weeks each. About 2 weeks after the last injection, the serum containing the antibody is isolated and tested as usual.

In a preferred embodiment, the antibody is a monoclonal antibody. For its preparation, spleen cells are removed from the mice after the above fourth injection and fused with myeloma cells as usual. The further cloning also takes place according to known methods.

By means of the present invention, it is possible to detect papilloma viruses, particularly in carcinomas of the skin. For this purpose, the DNA according to the invention can be used as such or when comprised by a further DNA. The latter may also be a papilloma virus genome or a portion thereof.

The present invention also enables the provision of formerly unknown papilloma viruses. They are found especially in carcinomas of the skin. In addition, the invention supplies proteins and virus-like particles which originate from these papilloma viruses. Moreover, antibodies are provided which are directed against these proteins and particles, respectively.

The present invention also enables to take diagnostic and therapeutic steps in the case of papilloma virus diseases. Moreover, it supplies the possibility of building up a vaccine against papilloma virus infections. Thus, the present invention represents a break-through in the field of papilloma virus research.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1

Identification of the Papilloma Virus Genome VS19-6-G

The total DNA is isolated from a biopsy of a squamous cell carcinoma of an immuno-suppressed person. 10 µg of this DNA are cleaved by the restriction enzyme BamHI and separated electrophoretically in a 0.5% agarose gel. At the same time, 10 µg of the above DNA, which was not cleaved, is also separated. The agarose gel is subjected to a blotting method so as to transfer the DNA from the agarose gel to a nitrocellulose membrane. It is employed in a hybridization method in which the above DNA of FIG. 1 is used in combination with the HP virus-65 DNA as $^{32}$P-labeled sample. Hybridization with the blotted DNA is obtained.

The person skilled in the field of DNA recombination technique is familiar with the above methods. Reference is made to Sambrook et al., supra, by way of supplement.

B. Example 2

Cloning of the Papilloma Virus Genome VS19-6-G.

The biopsy DNA obtained from Example 1 is cleaved by the restriction enzyme BamHI. The resulting fragments are used in a ligase reaction in which the dephosphorylated vector λZAP express cleaved by BamHI is also present. The resulting recombinant DNA molecules are packed in bacteriophages, and they are used for infecting bacteria. For these processing steps, the ZAP express vector kit offered by the company of Stratagene is used. The resulting phage plaques are then subjected to a hybridization process which uses the $^{32}$P-labeled DNA of FIG. 1 employed in Example 1 in combination with $^{32}$P-labeled HP virus-65 DNA. Hybridization with corresponding phage plaques is obtained. The BamHI fragments of VS19-6-G are isolated therefrom and used in a further ligase reaction together with a BamHI-cleaved, dephosphorylated plasmid vector, pBluescript. The resulting recombinant DNA molecules are used for transforming bacteria, *E. coli* XL1-Blue. By restriction cleavages and hybridization with the above DNA samples, respectively, a bacterial clone containing the papilloma virus genome VS19-6-G is identified. The plasmid of this bacterial clone is referred to as pBlue-VS19-6-G.

All references cited within the body of the instant specification are hereby incorporated by reference in their entirety.

What is claimed:

1. A polypeptide encoded by the nucleotide sequence of SEQ ID NO: 1, SEQ ID NO: 2, or SEQ ID NO: 3.

2. A polypeptide encoded by a polynucleotide hybridizing to the complement of the nucleotide sequence of SEQ ID NO: 1, SEQ ID NO: 2, or SEQ ID NO: 3, wherein the polynucleotide has at least 90% identity to the nucleotide sequence of SEQ ID NO: 1, SEQ ID NO: 2, or SEQ ID NO: 3.

3. An isolated polypeptide consisting of the amino acid sequence selected from the SEQ ID NO: 1, SEQ ID NO: 2, or SEQ ID NO: 3.

4. A composition comprising the polypeptide of any of the claims 1, 2, or 3 as reagent for diagnosis, treatment and/or vaccination, and a pharmaceutically acceptable carrier.

5. A pharmaceutical composition comprising the polypeptide of any of the claims 1, 2, or 3 and a pharmaceutically acceptable carrier.

6. A method of vaccinating a subject in need against papillomavirus, comprising administering to the subject the composition of claim 4.

7. A method of vaccinating a subject in need against papillomavirus, comprising administering to the subject the composition of claim 5.

8. A method of treating a subject in need against papillomavirus, comprising administering to the subject the composition of claim 4.

9. A method of treating a subject in need against papillomavirus, comprising administering to the subject the composition of claim 5.

10. A diagnostic kit to detect papillomavirus infection wherein the kit comprises the polypeptide of any of the claims 1, 2, or 3 as reagent for diagnosis.

* * * * *

SEQUENCE LISTING

```
<160> NUMBER OF SEQ ID NOS: 30

<210> SEQ ID NO 1
<211> LENGTH: 419
<212> TYPE: DNA
<213> ORGANISM: Papilloma virus
<220> FEATURE:
<221> NAME/KEY: CDS
<222> LOCATION: (1)...(417)

<400> SEQUENCE: 1 gga tcc atg cag gat ggt gac atg tgt gat ata gga ttc gga gct tgc      48
Gly Ser Met Gln Asp Gly Asp Met Cys Asp Ile Gly Phe Gly Ala Cys
 1               5                  10                  15 aat ttc agg gca ttt cag caa gat agg tca ggt gtt cct tta gat ata      96
Asn Phe Arg Ala Phe Gln Gln Asp Arg Ser Gly Val Pro Leu Asp Ile
            20                  25                  30 gta gat agt act tgc aag tat cca gac ttt ttg aaa atg aca aaa gac     144
Val Asp Ser Thr Cys Lys Tyr Pro Asp Phe Leu Lys Met Thr Lys Asp
        35                  40                  45 aag tat ggt gat gaa tgc ttc ttt ttt ggt cgt cga gag cag ttg tat     192
Lys Tyr Gly Asp Glu Cys Phe Phe Phe Gly Arg Arg Glu Gln Leu Tyr
    50                  55                  60 gca agg cat tat ttt acc aga gca ggc aca ata ggt gat tct att cca     240
Ala Arg His Tyr Phe Thr Arg Ala Gly Thr Ile Gly Asp Ser Ile Pro
65                  70                  75                  80 acg cca tat cag gaa tct gaa ttt tac aga tct cca cag gat agc cag     288
Thr Pro Tyr Gln Glu Ser Glu Phe Tyr Arg Ser Pro Gln Asp Ser Gln
                85                  90                  95 gct cag aat aat gtg gat tct cac att tat gta gcc act cct agt ggt     336
Ala Gln Asn Asn Val Asp Ser His Ile Tyr Val Ala Thr Pro Ser Gly
            100                 105                 110 tct tta act agc agt gat gct cag ctg ttt aac aga cct tat tgg ctc     384
Ser Leu Thr Ser Ser Asp Ala Gln Leu Phe Asn Arg Pro Tyr Trp Leu
        115                 120                 125 caa aat gct caa ggt acc aat aac gga atg gat cc                      419
Gln Asn Ala Gln Gly Thr Asn Asn Gly Met Asp
    130                 135

<210> SEQ ID NO 2
<211> LENGTH: 139
<212> TYPE: PRT
<213> ORGANISM: Papilloma virus

<400> SEQUENCE: 2

Gly Ser Met Gln Asp Gly Asp Met Cys Asp Ile Gly Phe Gly Ala Cys
 1               5                  10                  15

Asn Phe Arg Ala Phe Gln Gln Asp Arg Ser Gly Val Pro Leu Asp Ile
            20                  25                  30

Val Asp Ser Thr Cys Lys Tyr Pro Asp Phe Leu Lys Met Thr Lys Asp
        35                  40                  45

Lys Tyr Gly Asp Glu Cys Phe Phe Phe Gly Arg Arg Glu Gln Leu Tyr
    50                  55                  60

Ala Arg His Tyr Phe Thr Arg Ala Gly Thr Ile Gly Asp Ser Ile Pro
65                  70                  75                  80
```

```
Thr Pro Tyr Gln Glu Ser Glu Phe Tyr Arg Ser Pro Gln Asp Ser Gln
             85                  90                  95

Ala Gln Asn Asn Val Asp Ser His Ile Tyr Val Ala Thr Pro Ser Gly
            100                 105                 110

Ser Leu Thr Ser Ser Asp Ala Gln Leu Phe Asn Arg Pro Tyr Trp Leu
            115                 120                 125

Gln Asn Ala Gln Gly Thr Asn Asn Gly Met Asp
        130                 135

<210> SEQ ID NO 3
<211> LENGTH: 419
<212> TYPE: DNA
<213> ORGANISM: Papilloma virus

<400> SEQUENCE: 3
ggatccattc cgttattggt accttgagca ttttggagcc aataaggtct gttaaacagc      60
tgagcatcac tgctagttaa agaaccacta ggagtggcta cataaatgtg agaatccaca    120
ttattctgag cctggctatc ctgtggagat ctgtaaaatt cagattcctg atatggcgtt    180
ggaatagaat cacctattgt gcctgctctg gtaaataat gccttgcata caactgctct     240
cgacgaccaa aaagaagca ttcatcacca tacttgtctt ttgtcatttt caaaaagtct     300
ggatacttgc aagtactatc tactatatct aaaggaacac ctgacctatc ttgctgaaat    360
gccctgaaat tgcaagctcc gaatcctata tcacacatgt caccatcctg catggatcc    419

<210> SEQ ID NO 4
<211> LENGTH: 434
<212> TYPE: DNA
<213> ORGANISM: Papilloma virus
<220> FEATURE:
<221> NAME/KEY: CDS
<222> LOCATION: (1)...(432)

<400> SEQUENCE: 4 gga tcc atg gag gac ggt gag atg gca gac ata gga tat ggt aat ctt      48
Gly Ser Met Glu Asp Gly Glu Met Ala Asp Ile Gly Tyr Gly Asn Leu
  1               5                  10                  15 aat ttt aaa gct tta cag gaa aat agg cct gat gtt agt ctt gat att      96
Asn Phe Lys Ala Leu Gln Glu Asn Arg Pro Asp Val Ser Leu Asp Ile
             20                  25                  30 gtc aat gaa acc tgc aaa tat cca gat ttt ttg aag atg caa aat gat     144
Val Asn Glu Thr Cys Lys Tyr Pro Asp Phe Leu Lys Met Gln Asn Asp
         35                  40                  45 gtt tat gga gac tcc tgt ttc ttt ttt gct cgt aga gag caa tgt tat     192
Val Tyr Gly Asp Ser Cys Phe Phe Phe Ala Arg Arg Glu Gln Cys Tyr
     50                  55                  60 gcc aga cac ttt ttt gta aga ggt ggc aac gta ggg gat gac att cct     240
Ala Arg His Phe Phe Val Arg Gly Gly Asn Val Gly Asp Asp Ile Pro
 65                  70                  75                  80 ggt gaa caa ata gac gca ggc aca tat aaa aat gat ttt tac att cca     288
Gly Glu Gln Ile Asp Ala Gly Thr Tyr Lys Asn Asp Phe Tyr Ile Pro
                 85                  90                  95 gga gca tca ggt cag aca caa aat aaa ata ggt aac tcc atg tat ttc     336
Gly Ala Ser Gly Gln Thr Gln Asn Lys Ile Gly Asn Ser Met Tyr Phe
            100                 105                 110 cca aca gtt agt ggc tca tta gtg tct agt gat gct cag ctg ttt aat     384
Pro Thr Val Ser Gly Ser Leu Val Ser Ser Asp Ala Gln Leu Phe Asn
            115                 120                 125 agg ccc tac tgg ctc caa cgc gca cag ggc cac aac aac ggc gtg gat     432
Arg Pro Tyr Trp Leu Gln Arg Ala Gln Gly His Asn Asn Gly Val Asp
```

```
                    130              135              140
cc                                                                              434
```

<210> SEQ ID NO 5
<211> LENGTH: 144
<212> TYPE: PRT
<213> ORGANISM: Papilloma virus

<400> SEQUENCE: 5

```
Gly Ser Met Glu Asp Gly Glu Met Ala Asp Ile Gly Tyr Gly Asn Leu
 1               5                  10                  15

Asn Phe Lys Ala Leu Gln Glu Asn Arg Pro Asp Val Ser Leu Asp Ile
             20                  25                  30

Val Asn Glu Thr Cys Lys Tyr Pro Asp Phe Leu Lys Met Gln Asn Asp
         35                  40                  45

Val Tyr Gly Asp Ser Cys Phe Phe Ala Arg Arg Glu Gln Cys Tyr
     50                  55                  60

Ala Arg His Phe Phe Val Arg Gly Asn Val Gly Asp Asp Ile Pro
 65                  70                  75                  80

Gly Glu Gln Ile Asp Ala Gly Thr Tyr Lys Asn Asp Phe Tyr Ile Pro
                 85                  90                  95

Gly Ala Ser Gly Gln Thr Gln Asn Lys Ile Gly Asn Ser Met Tyr Phe
            100                 105                 110

Pro Thr Val Ser Gly Ser Leu Val Ser Ser Asp Ala Gln Leu Phe Asn
            115                 120                 125

Arg Pro Tyr Trp Leu Gln Arg Ala Gln Gly His Asn Asn Gly Val Asp
            130                 135                 140
```

<210> SEQ ID NO 6
<211> LENGTH: 434
<212> TYPE: DNA
<213> ORGANISM: Papilloma virus

<400> SEQUENCE: 6

```
ggatccacgc cgttgttgtg gccctgtgcg cgttggagcc agtagggcct attaaacagc     60
tgagcatcac tagacactaa tgagccacta actgttggga aatacatgga gttacctatt    120
ttattttgtg tctgacctga tgctcctgga atgtaaaaat cattttata tgtgcctgcg    180 tctatttgtt caccaggaat gtcatcccct acgttgccac ctcttacaaa aaagtgtctg    240
gcataacatt gctctctacg agcaaaaaag aaacaggagt ctccataaac atcattttgc    300
atcttcaaaa aatctggata tttgcaggtt tcattgacaa tatcaagact aacatcaggc    360 ctatttttcct gtaaagcttt aaaattaaga ttaccatatc ctatgtctgc catctcaccg    420
tcctccatgg atcc                                                      434
```

<210> SEQ ID NO 7
<211> LENGTH: 410
<212> TYPE: DNA
<213> ORGANISM: Papilloma virus
<220> FEATURE:
<221> NAME/KEY: CDS
<222> LOCATION: (1)...(408)

<400> SEQUENCE: 7

```
gga tcc cta gag gat ggt gat atg ggt gat ata gga ttt ggg cat gct     48
Gly Ser Leu Glu Asp Gly Asp Met Gly Asp Ile Gly Phe Gly His Ala
 1               5                  10                  15 aat ttt agc cgt tta caa gaa gat aaa gca ggt gtg cca tta gaa tta     96
```

```
Asn Phe Ser Arg Leu Gln Glu Asp Lys Ala Gly Val Pro Leu Glu Leu
             20                  25                  30 gtg gac act ttt agt ata tgg cct gac ttt tta cgc atg acc agt gat       144
Val Asp Thr Phe Ser Ile Trp Pro Asp Phe Leu Arg Met Thr Ser Asp
         35                  40                  45 ata tat gga gat gct gtg ttt ttt tgg gga aag cga gaa cat atg ttt       192
Ile Tyr Gly Asp Ala Val Phe Phe Trp Gly Lys Arg Glu His Met Phe
 50                  55                  60 gcc aga cat tta tgg gca aga gct gga act atg ggc gac gct att cca       240
Ala Arg His Leu Trp Ala Arg Ala Gly Thr Met Gly Asp Ala Ile Pro
 65                  70                  75                  80 gat aat aat gca gag ttt ttt ctg cat ccc aat ggt gca cct caa aat       288
Asp Asn Asn Ala Glu Phe Phe Leu His Pro Asn Gly Ala Pro Gln Asn
             85                  90                  95 aag tta gcc tca ttt gct tat ttt cca aca cct agt ggt tct ctt aat       336
Lys Leu Ala Ser Phe Ala Tyr Phe Pro Thr Pro Ser Gly Ser Leu Asn
            100                 105                 110 acc agt gat aat caa ttg ttt aat aag ccg tat tgg ttg cga aaa gct       384
Thr Ser Asp Asn Gln Leu Phe Asn Lys Pro Tyr Trp Leu Arg Lys Ala
            115                 120                 125 cag ggc acc aac aat ggg atg gat cc                                    410
Gln Gly Thr Asn Asn Gly Met Asp
            130                 135

<210> SEQ ID NO 8
<211> LENGTH: 136
<212> TYPE: PRT
<213> ORGANISM: Papilloma virus

<400> SEQUENCE: 8

Gly Ser Leu Glu Asp Gly Asp Met Gly Asp Ile Gly Phe Gly His Ala
 1               5                  10                  15

Asn Phe Ser Arg Leu Gln Glu Asp Lys Ala Gly Val Pro Leu Glu Leu
             20                  25                  30

Val Asp Thr Phe Ser Ile Trp Pro Asp Phe Leu Arg Met Thr Ser Asp
         35                  40                  45

Ile Tyr Gly Asp Ala Val Phe Phe Trp Gly Lys Arg Glu His Met Phe
 50                  55                  60

Ala Arg His Leu Trp Ala Arg Ala Gly Thr Met Gly Asp Ala Ile Pro
 65                  70                  75                  80

Asp Asn Asn Ala Glu Phe Phe Leu His Pro Asn Gly Ala Pro Gln Asn
             85                  90                  95

Lys Leu Ala Ser Phe Ala Tyr Phe Pro Thr Pro Ser Gly Ser Leu Asn
            100                 105                 110

Thr Ser Asp Asn Gln Leu Phe Asn Lys Pro Tyr Trp Leu Arg Lys Ala
            115                 120                 125

Gln Gly Thr Asn Asn Gly Met Asp
            130                 135

<210> SEQ ID NO 9
<211> LENGTH: 410
<212> TYPE: DNA
<213> ORGANISM: Papilloma virus

<400> SEQUENCE: 9
ggatccatcc cattgttggt gccctgagct tttcgcaacc aatacggctt attaaacaat      60
tgattatcac tggtattaag agaaccacta ggtgttggaa aataagcaaa tgaggctaac     120
ttattttgag gtgcaccatt gggatgcaga aaaaactctg cattattatc tggaatagcg     180
```

```
tcgcccatag ttccagctct tgcccataaa tgtctggcaa acatatgttc tcgctttccc      240
caaaaaaaca cagcatctcc atatatatca ctggtcatgc gtaaaaagtc aggccatata      300
ctaaaagtgt ccactaattc taatggcaca cctgctttat cttcttgtaa acggctaaaa      360
ttagcatgcc caaatcctat atcacccata tcaccatcct ctagggatcc                 410
```

```
<210> SEQ ID NO 10
<211> LENGTH: 437
<212> TYPE: DNA
<213> ORGANISM: Papilloma virus
<220> FEATURE:
<221> NAME/KEY: CDS
<222> LOCATION: (1)...(435)

<400> SEQUENCE: 10
```

```
gga tcc att gag gat gcg gat atg agt gat ata gga ttt gga gct gtg       48
Gly Ser Ile Glu Asp Ala Asp Met Ser Asp Ile Gly Phe Gly Ala Val
 1               5                  10                  15 aat ttt agc act ttc tct gaa agc cgg gct gat gca cct tta gaa tta       96
Asn Phe Ser Thr Phe Ser Glu Ser Arg Ala Asp Ala Pro Leu Glu Leu
                20                  25                  30 atc aat tct att agt aaa tgg cct gat ttt att caa atg tct aag gat      144
Ile Asn Ser Ile Ser Lys Trp Pro Asp Phe Ile Gln Met Ser Lys Asp
             35                  40                  45 att tat ggc gat aga atg ttt ttc ttt gga aaa cgt gag cag atg tat      192
Ile Tyr Gly Asp Arg Met Phe Phe Phe Gly Lys Arg Glu Gln Met Tyr
 50                  55                  60 gca aga cac aca ttt tgt aaa gat ggt gct gtg gga gat gct att cca      240
Ala Arg His Thr Phe Cys Lys Asp Gly Ala Val Gly Asp Ala Ile Pro
 65                  70                  75                  80 gaa aat tta aat aat gat gag gat gtt cat cat agg ttt tta tta aat      288
Glu Asn Leu Asn Asn Asp Glu Asp Val His His Arg Phe Leu Leu Asn
                 85                  90                  95 cct aag cct gac gca cca cca tat tca aac tta gga aac agt act tac      336
Pro Lys Pro Asp Ala Pro Pro Tyr Ser Asn Leu Gly Asn Ser Thr Tyr
            100                 105                 110 ttt cct atg cca agt ggt tca tta gtt agt agt gaa act caa tta ttt      384
Phe Pro Met Pro Ser Gly Ser Leu Val Ser Ser Glu Thr Gln Leu Phe
        115                 120                 125 aac aga cca ttt tgg cta cat cga gca cag ggc acc aat aac ggc atg      432
Asn Arg Pro Phe Trp Leu His Arg Ala Gln Gly Thr Asn Asn Gly Met
    130                 135                 140 gat cc                                                                437
Asp
145
```

```
<210> SEQ ID NO 11
<211> LENGTH: 145
<212> TYPE: PRT
<213> ORGANISM: Papilloma virus

<400> SEQUENCE: 11
```

```
Gly Ser Ile Glu Asp Ala Asp Met Ser Asp Ile Gly Phe Gly Ala Val
 1               5                  10                  15

Asn Phe Ser Thr Phe Ser Glu Ser Arg Ala Asp Ala Pro Leu Glu Leu
                20                  25                  30

Ile Asn Ser Ile Ser Lys Trp Pro Asp Phe Ile Gln Met Ser Lys Asp
             35                  40                  45

Ile Tyr Gly Asp Arg Met Phe Phe Phe Gly Lys Arg Glu Gln Met Tyr
 50                  55                  60
```

```
Ala Arg His Thr Phe Cys Lys Asp Gly Ala Val Gly Asp Ala Ile Pro
 65                  70                  75                  80

Glu Asn Leu Asn Asn Asp Glu Asp Val His His Arg Phe Leu Leu Asn
             85                  90                  95

Pro Lys Pro Asp Ala Pro Pro Tyr Ser Asn Leu Gly Asn Ser Thr Tyr
            100                 105                 110

Phe Pro Met Pro Ser Gly Ser Leu Val Ser Ser Glu Thr Gln Leu Phe
            115                 120                 125

Asn Arg Pro Phe Trp Leu His Arg Ala Gln Gly Thr Asn Asn Gly Met
        130                 135                 140

Asp
145

<210> SEQ ID NO 12
<211> LENGTH: 437
<212> TYPE: DNA
<213> ORGANISM: Papilloma virus

<400> SEQUENCE: 12
ggatccatgc cgttattggt gccctgtgct cgatgtagcc aaaatggtct gttaaataat    60
tgagtttcac tactaactaa tgaaccactt ggcataggaa agtaagtact gtttcctaag   120
tttgaatatg gtggtgcgtc aggcttagga tttaataaaa acctatgatg aacatcctca   180
tcattattta aattttctgg aatagcatct cccacagcac catctttaca aaatgtgtgt   240
cttgcataca tctgctcacg ttttccaaag aaaaacattc tatcgccata aatatcctta   300
gacatttgaa taaaatcagg ccatttacta atagaattga ttaattctaa aggtgcatca   360
gcccggcttt cagagaaagt gctaaaattc acagctccaa atcctatatc actcatatcc   420
gcatcctcaa tggatcc                                                  437

<210> SEQ ID NO 13
<211> LENGTH: 416
<212> TYPE: DNA
<213> ORGANISM: Papilloma virus
<220> FEATURE:
<221> NAME/KEY: CDS
<222> LOCATION: (1)...(414)

<400> SEQUENCE: 13 gga tcc atg gag gat ggt gaa atg ggc gac ata ggc ttt gga gcc ttt     48
Gly Ser Met Glu Asp Gly Glu Met Gly Asp Ile Gly Phe Gly Ala Phe
  1               5                  10                  15 aat ttt aaa gcc cta cag aaa gat cgt gct ggt gtt agt tta gat tta     96
Asn Phe Lys Ala Leu Gln Lys Asp Arg Ala Gly Val Ser Leu Asp Leu
             20                  25                  30 gtt gat aca ttc agt ata tgg cca gac ttt tta aaa atg act aat gat    144
Val Asp Thr Phe Ser Ile Trp Pro Asp Phe Leu Lys Met Thr Asn Asp
         35                  40                  45 ata tat ggt gac agt atc ttt ttt tat ggt aaa aga gaa cag cta ttt    192
Ile Tyr Gly Asp Ser Ile Phe Phe Tyr Gly Lys Arg Glu Gln Leu Phe
     50                  55                  60 agt aga cac ttg tgg gcc cgc gca gga acg gct gga gat gcc att cca    240
Ser Arg His Leu Trp Ala Arg Ala Gly Thr Ala Gly Asp Ala Ile Pro
 65                  70                  75                  80 tct cct gat aac aaa aat cta ata ttt cag ggt gat gat gca gtg cca    288
Ser Pro Asp Asn Lys Asn Leu Ile Phe Gln Gly Asp Asp Ala Val Pro
             85                  90                  95 caa aag act gct ggg tct ttt act tat ttt agt gcc cct agt ggg tca    336
```

```
Gln Lys Thr Ala Gly Ser Phe Thr Tyr Phe Ser Ala Pro Ser Gly Ser
            100                 105                 110 tta aca act agt gat tct cag tta ttt aat agg cca tat tgg tta aga    384
Leu Thr Thr Ser Asp Ser Gln Leu Phe Asn Arg Pro Tyr Trp Leu Arg
        115                 120                 125 aga gct caa ggt acc aac aac ggt gtg gat cc                         416
Arg Ala Gln Gly Thr Asn Asn Gly Val Asp
    130                 135

<210> SEQ ID NO 14
<211> LENGTH: 138
<212> TYPE: PRT
<213> ORGANISM: Papilloma virus

<400> SEQUENCE: 14

Gly Ser Met Glu Asp Gly Glu Met Gly Asp Ile Gly Phe Gly Ala Phe
1               5                   10                  15

Asn Phe Lys Ala Leu Gln Lys Asp Arg Ala Gly Val Ser Leu Asp Leu
            20                  25                  30

Val Asp Thr Phe Ser Ile Trp Pro Asp Phe Leu Lys Met Thr Asn Asp
        35                  40                  45

Ile Tyr Gly Asp Ser Ile Phe Phe Tyr Gly Lys Arg Glu Gln Leu Phe
    50                  55                  60

Ser Arg His Leu Trp Ala Arg Ala Gly Thr Ala Gly Asp Ala Ile Pro
65                  70                  75                  80

Ser Pro Asp Asn Lys Asn Leu Ile Phe Gln Gly Asp Asp Ala Val Pro
                85                  90                  95

Gln Lys Thr Ala Gly Ser Phe Thr Tyr Phe Ser Ala Pro Ser Gly Ser
            100                 105                 110

Leu Thr Thr Ser Asp Ser Gln Leu Phe Asn Arg Pro Tyr Trp Leu Arg
        115                 120                 125

Arg Ala Gln Gly Thr Asn Asn Gly Val Asp
    130                 135

<210> SEQ ID NO 15
<211> LENGTH: 416
<212> TYPE: DNA
<213> ORGANISM: Papilloma virus

<400> SEQUENCE: 15
ggatccacac cgttgttggt accttgagct cttcttaacc aatatggcct attaaataac     60
tgagaatcac tagttgttaa tgacccacta ggggcactaa aataagtaaa agacccagca    120
gtcttttgtg gcactgcatc atcaccctga aatattagat ttttgttatc aggagatgga    180
atggcatctc cagccgttcc tgcgcgggcc cacaagtgtc tactaaatag ctgttctctt    240
ttaccataaa aaaagatact gtcaccatat atatcattag tcattttttaa aaagtctggc    300 catatactga atgtatcaac taaatctaaa ctaacaccag cacgatcttt ctgtagggct    360
ttaaaattaa aggctccaaa gcctatgtcg cccatttcac catcctccat ggatcc        416

<210> SEQ ID NO 16
<211> LENGTH: 413
<212> TYPE: DNA
<213> ORGANISM: Papilloma virus
<220> FEATURE:
<221> NAME/KEY: CDS
<222> LOCATION: (1)...(411)

<400> SEQUENCE: 16
```

```
gga tcc atg gag gac ggt gag atg agt gat aca ggt ttt ggt gct atg         48
Gly Ser Met Glu Asp Gly Glu Met Ser Asp Thr Gly Phe Gly Ala Met
 1               5                  10                  15 aat ttt gat aat cta tgc gag gac aga gct tca ttt cct tta gac att         96
Asn Phe Asp Asn Leu Cys Glu Asp Arg Ala Ser Phe Pro Leu Asp Ile
             20                  25                  30 ata aat gag acc tcc aag tgg cct gat ttt cta aaa atg aat aaa gat        144
Ile Asn Glu Thr Ser Lys Trp Pro Asp Phe Leu Lys Met Asn Lys Asp
         35                  40                  45 cct tat gga gat cat ata ttt ttc ttt ggt tta cga gag cag tta tat        192
Pro Tyr Gly Asp His Ile Phe Phe Phe Gly Leu Arg Glu Gln Leu Tyr
     50                  55                  60 tcc aga cat cat ggt gct cgg gga gga aaa atg gga gat act att cca        240
Ser Arg His His Gly Ala Arg Gly Gly Lys Met Gly Asp Thr Ile Pro
 65                  70                  75                  80 gaa aat aca gca ggc gaa tat tat tat cct cct act gat ggt gct cag        288
Glu Asn Thr Ala Gly Glu Tyr Tyr Tyr Pro Pro Thr Asp Gly Ala Gln
                 85                  90                  95 caa aat ata ggt tca cat att tat ttc aat act gtt agt gga tct tta        336
Gln Asn Ile Gly Ser His Ile Tyr Phe Asn Thr Val Ser Gly Ser Leu
            100                 105                 110 aca tct tca gaa act cag ata ttt aat agg cca tat ttt tta caa cgt        384
Thr Ser Ser Glu Thr Gln Ile Phe Asn Arg Pro Tyr Phe Leu Gln Arg
        115                 120                 125 gca cag ggc aca aac aac gga gtg gat cc                                 413
Ala Gln Gly Thr Asn Asn Gly Val Asp
    130                 135
```

<210> SEQ ID NO 17
<211> LENGTH: 137
<212> TYPE: PRT
<213> ORGANISM: Papilloma virus

<400> SEQUENCE: 17

```
Gly Ser Met Glu Asp Gly Glu Met Ser Asp Thr Gly Phe Gly Ala Met
 1               5                  10                  15

Asn Phe Asp Asn Leu Cys Glu Asp Arg Ala Ser Phe Pro Leu Asp Ile
             20                  25                  30

Ile Asn Glu Thr Ser Lys Trp Pro Asp Phe Leu Lys Met Asn Lys Asp
         35                  40                  45

Pro Tyr Gly Asp His Ile Phe Phe Phe Gly Leu Arg Glu Gln Leu Tyr
     50                  55                  60

Ser Arg His His Gly Ala Arg Gly Gly Lys Met Gly Asp Thr Ile Pro
 65                  70                  75                  80

Glu Asn Thr Ala Gly Glu Tyr Tyr Tyr Pro Pro Thr Asp Gly Ala Gln
                 85                  90                  95

Gln Asn Ile Gly Ser His Ile Tyr Phe Asn Thr Val Ser Gly Ser Leu
            100                 105                 110

Thr Ser Ser Glu Thr Gln Ile Phe Asn Arg Pro Tyr Phe Leu Gln Arg
        115                 120                 125

Ala Gln Gly Thr Asn Asn Gly Val Asp
    130                 135
```

<210> SEQ ID NO 18
<211> LENGTH: 413
<212> TYPE: DNA
<213> ORGANISM: Papilloma virus

<400> SEQUENCE: 18

-continued

```
ggatccactc cgttgtttgt gccctgtgca cgttgtaaaa aatatggcct attaaatatc      60
tgagtttctg aagatgttaa agatccacta acagtattga aataaatatg tgaacctata     120
ttttgctgag caccatcagt aggaggataa taatattcgc ctgctgtatt ttctggaata     180
gtatctccca tttttcctcc ccgagcacca tgatgtctgg aatataactg ctctcgtaaa     240
ccaaagaaaa atatatgatc tccataagga tctttattca tttttagaaa atcaggccac     300
ttggaggtct catttataat gtctaaagga aatgaagctc tgtcctcgca tagattatca     360
aaattcatag caccaaaacc tgtatcactc atctcaccgt cctccatgga tcc            413
```

```
<210> SEQ ID NO 19
<211> LENGTH: 428
<212> TYPE: DNA
<213> ORGANISM: Papilloma virus
<220> FEATURE:
<221> NAME/KEY: CDS
<222> LOCATION: (1)...(426)

<400> SEQUENCE: 19
```

```
gga tcc att caa gat ggg gat atg tgc gat att ggc ttt gga gca gcc        48
Gly Ser Ile Gln Asp Gly Asp Met Cys Asp Ile Gly Phe Gly Ala Ala
 1               5                  10                  15 aat ttt aaa gca tta cag caa gat aaa tca ggt gtt cct tta gat att        96
Asn Phe Lys Ala Leu Gln Gln Asp Lys Ser Gly Val Pro Leu Asp Ile
            20                  25                  30 gtt gac agt ata tgt aaa tgg cca gat att att aaa atg gag caa gaa       144
Val Asp Ser Ile Cys Lys Trp Pro Asp Ile Ile Lys Met Glu Gln Glu
        35                  40                  45 ata tat gga gac aga tta ttt ttc ttt act aaa cgt gag caa gct tat       192
Ile Tyr Gly Asp Arg Leu Phe Phe Phe Thr Lys Arg Glu Gln Ala Tyr
    50                  55                  60 gcc agg cat tat ttc gct cgt gca gga att aat ggt gat tct tta cca       240
Ala Arg His Tyr Phe Ala Arg Ala Gly Ile Asn Gly Asp Ser Leu Pro
65                  70                  75                  80 gat gca atg aaa cca gga gaa tat tat ctc tct cct aag ttg gga gat       288
Asp Ala Met Lys Pro Gly Glu Tyr Tyr Leu Ser Pro Lys Leu Gly Asp
                85                  90                  95 gag caa gta ccc cag aaa gac tta gga tcg cat att tat ttt cct aca       336
Glu Gln Val Pro Gln Lys Asp Leu Gly Ser His Ile Tyr Phe Pro Thr
            100                 105                 110 gtt agt ggt tct ttg gtt tct agt gaa aat cag tta ttt aac aga cca       384
Val Ser Gly Ser Leu Val Ser Ser Glu Asn Gln Leu Phe Asn Arg Pro
        115                 120                 125 tat tgg ttg cag aaa tct cag ggc aca aac aac ggc gtg gat                426
Tyr Trp Leu Gln Lys Ser Gln Gly Thr Asn Asn Gly Val Asp
    130                 135                 140 cc                                                                     428
```

```
<210> SEQ ID NO 20
<211> LENGTH: 142
<212> TYPE: PRT
<213> ORGANISM: Papilloma virus

<400> SEQUENCE: 20
```

```
Gly Ser Ile Gln Asp Gly Asp Met Cys Asp Ile Gly Phe Gly Ala Ala
 1               5                  10                  15

Asn Phe Lys Ala Leu Gln Gln Asp Lys Ser Gly Val Pro Leu Asp Ile
            20                  25                  30

Val Asp Ser Ile Cys Lys Trp Pro Asp Ile Ile Lys Met Glu Gln Glu
        35                  40                  45
```

```
Ile Tyr Gly Asp Arg Leu Phe Phe Thr Lys Arg Glu Gln Ala Tyr
 50                   55                  60

Ala Arg His Tyr Phe Ala Arg Ala Gly Ile Asn Gly Asp Ser Leu Pro
 65                  70                  75                  80

Asp Ala Met Lys Pro Gly Glu Tyr Tyr Leu Ser Pro Lys Leu Gly Asp
                 85                  90                  95

Glu Gln Val Pro Gln Lys Asp Leu Gly Ser His Ile Tyr Phe Pro Thr
                100                 105                 110

Val Ser Gly Ser Leu Val Ser Ser Glu Asn Gln Leu Phe Asn Arg Pro
                115                 120                 125

Tyr Trp Leu Gln Lys Ser Gln Gly Thr Asn Asn Gly Val Asp
130                 135                 140

<210> SEQ ID NO 21
<211> LENGTH: 428
<212> TYPE: DNA
<213> ORGANISM: Papilloma virus

<400> SEQUENCE: 21
ggatccacgc cgttgtttgt gccctgagat ttctgcaacc aatatggtct gttaaataac      60
tgattttcac tagaaaccaa agaaccacta actgtaggaa aataaatatg cgatcctaag    120
tctttctggg gtacttgctc atctcccaac ttaggagaga gataatattc tcctggtttc    180
attgcatctg gtaaagaatc accattaatt cctgcacgag cgaaataatg cctggcataa    240
gcttgctcac gtttagtaaa gaaaaataat ctgtctccat atatttcttg ctccatttta    300
ataatatctg gccatttaca tatactgtca acaatatcta aaggaacacc tgatttatct    360
tgctgtaatg ctttaaaatt ggctgctcca aagccaatat cgcacatatc cccatcttga    420
atggatcc                                                              428

<210> SEQ ID NO 22
<211> LENGTH: 416
<212> TYPE: DNA
<213> ORGANISM: Papilloma virus
<220> FEATURE:
<221> NAME/KEY: CDS
<222> LOCATION: (1)...(414)

<400> SEQUENCE: 22 gga tcc ctg gaa gat ggt gaa atg gga gat att ggg ttt ggt gca gca      48
Gly Ser Leu Glu Asp Gly Glu Met Gly Asp Ile Gly Phe Gly Ala Ala
 1               5                  10                  15 aat ttt aaa acg tta caa aag gac aga gcc gga gtc agc tta gat tta      96
Asn Phe Lys Thr Leu Gln Lys Asp Arg Ala Gly Val Ser Leu Asp Leu
                20                  25                  30 gta gac act ttt agc att tgg cct gac ttt tta aaa atg act aat gat     144
Val Asp Thr Phe Ser Ile Trp Pro Asp Phe Leu Lys Met Thr Asn Asp
             35                  40                  45 att tac gga gat agt atg ttt ttc ttt gga aaa cgt gag cag ctc ttt     192
Ile Tyr Gly Asp Ser Met Phe Phe Phe Gly Lys Arg Glu Gln Leu Phe
         50                  55                  60 ggc aga cat ctt tgg aca aga gca ggt act ccc ggc gat gca att cct     240
Gly Arg His Leu Trp Thr Arg Ala Gly Thr Pro Gly Asp Ala Ile Pro
 65                  70                  75                  80 act cca gaa aat ata aac tta ata ttt cca gct gat gat ggc act agt     288
Thr Pro Glu Asn Ile Asn Leu Ile Phe Pro Ala Asp Asp Gly Thr Ser
                 85                  90                  95 caa aag gat gca ggg tct ttc act tac ttt act tca gct agt gga tct     336
```

```
Gln Lys Asp Ala Gly Ser Phe Tyr Phe Thr Ser Ala Ser Gly Ser
            100                 105                 110 ctt aat act agc gat tca caa tta ttt aat aga cct tac tgg ctt cga        384
Leu Asn Thr Ser Asp Ser Gln Leu Phe Asn Arg Pro Tyr Trp Leu Arg
        115                 120                 125 cgt gca caa ggc aca aac aat ggc gtg gat cc                             416
Arg Ala Gln Gly Thr Asn Asn Gly Val Asp
    130                 135
```

<210> SEQ ID NO 23
<211> LENGTH: 138
<212> TYPE: PRT
<213> ORGANISM: Papilloma virus

<400> SEQUENCE: 23

```
Gly Ser Leu Glu Asp Gly Glu Met Gly Asp Ile Gly Phe Gly Ala Ala
1               5                   10                  15

Asn Phe Lys Thr Leu Gln Lys Asp Arg Ala Gly Val Ser Leu Asp Leu
            20                  25                  30

Val Asp Thr Phe Ser Ile Trp Pro Asp Phe Leu Lys Met Thr Asn Asp
        35                  40                  45

Ile Tyr Gly Asp Ser Met Phe Phe Gly Lys Arg Glu Gln Leu Phe
    50                  55                  60

Gly Arg His Leu Trp Thr Arg Ala Gly Thr Pro Gly Asp Ala Ile Pro
65                  70                  75                  80

Thr Pro Glu Asn Ile Asn Leu Ile Phe Pro Ala Asp Asp Gly Thr Ser
                85                  90                  95

Gln Lys Asp Ala Gly Ser Phe Tyr Phe Thr Ser Ala Ser Gly Ser
            100                 105                 110

Leu Asn Thr Ser Asp Ser Gln Leu Phe Asn Arg Pro Tyr Trp Leu Arg
        115                 120                 125

Arg Ala Gln Gly Thr Asn Asn Gly Val Asp
    130                 135
```

<210> SEQ ID NO 24
<211> LENGTH: 416
<212> TYPE: DNA
<213> ORGANISM: Papilloma virus

<400> SEQUENCE: 24

```
ggatccacgc cattgtttgt gccttgtgca cgtcgaagcc agtaaggtct attaaataat      60
tgtgaatcgc tagtattaag agatccacta gctgaagtaa agtaagtgaa agaccctgca    120
tccttttgac tagtgccatc atcagctgga aatattaagt ttatattttc tggagtagga    180
attgcatcgc cgggagtacc tgctcttgtc caaagatgtc tgccaaagag ctgctcacgt    240
tttccaaaga aaacatact atctccgtaa atatcattag tcattttaa aaagtcaggc      300
caaatgctaa aagtgtctac taaatctaag ctgactccgg ctctgtcctt ttgtaacgtt    360
ttaaatttg ctgcaccaaa cccaatatct cccatttcac catcttccag ggatcc         416
```

<210> SEQ ID NO 25
<211> LENGTH: 425
<212> TYPE: DNA
<213> ORGANISM: Papilloma virus
<220> FEATURE:
<221> NAME/KEY: CDS
<222> LOCATION: (1)...(423)

<400> SEQUENCE: 25

```
gga tcc cta gag gat ggg gag atg ggt gat ata gga ttt ggt gct gct    48
Gly Ser Leu Glu Asp Gly Glu Met Gly Asp Ile Gly Phe Gly Ala Ala
 1               5                  10                  15 aat ttt gct aag ctt atg caa gat aga gct ggt gta cct ctg gaa tta    96
Asn Phe Ala Lys Leu Met Gln Asp Arg Ala Gly Val Pro Leu Glu Leu
             20                  25                  30 ata gat agt att agt ata tgg cca gat ttt cta aaa atg aca aag gat   144
Ile Asp Ser Ile Ser Ile Trp Pro Asp Phe Leu Lys Met Thr Lys Asp
         35                  40                  45 att tat gga aat gaa gta ttt ttc ttt gga aaa cgc gag caa tgt tat   192
Ile Tyr Gly Asn Glu Val Phe Phe Phe Gly Lys Arg Glu Gln Cys Tyr
     50                  55                  60 gct cgc cat tta ttt gcc aga gct ggt act atg gga gaa cca gta cct   240
Ala Arg His Leu Phe Ala Arg Ala Gly Thr Met Gly Glu Pro Val Pro
 65                  70                  75                  80 aat gag act aat gga gta aat ttt ata aat gca aaa cca gga gat cca   288
Asn Glu Thr Asn Gly Val Asn Phe Ile Asn Ala Lys Pro Gly Asp Pro
                 85                  90                  95 aat ccc agg agc gct cat atg ggt tct tca gta tac ttt gca aca cct   336
Asn Pro Arg Ser Ala His Met Gly Ser Ser Val Tyr Phe Ala Thr Pro
            100                 105                 110 agt ggc tcc ctt aat acc agt gat tca caa ata ttt aac aga cct tat   384
Ser Gly Ser Leu Asn Thr Ser Asp Ser Gln Ile Phe Asn Arg Pro Tyr
            115                 120                 125 tgg tta cga cgg gct caa gga acg aac aac ggc atg gat cc            425
Trp Leu Arg Arg Ala Gln Gly Thr Asn Asn Gly Met Asp
            130                 135                 140

<210> SEQ ID NO 26
<211> LENGTH: 141
<212> TYPE: PRT
<213> ORGANISM: Papilloma virus

<400> SEQUENCE: 26

Gly Ser Leu Glu Asp Gly Glu Met Gly Asp Ile Gly Phe Gly Ala Ala
 1               5                  10                  15

Asn Phe Ala Lys Leu Met Gln Asp Arg Ala Gly Val Pro Leu Glu Leu
             20                  25                  30

Ile Asp Ser Ile Ser Ile Trp Pro Asp Phe Leu Lys Met Thr Lys Asp
         35                  40                  45

Ile Tyr Gly Asn Glu Val Phe Phe Phe Gly Lys Arg Glu Gln Cys Tyr
     50                  55                  60

Ala Arg His Leu Phe Ala Arg Ala Gly Thr Met Gly Glu Pro Val Pro
 65                  70                  75                  80

Asn Glu Thr Asn Gly Val Asn Phe Ile Asn Ala Lys Pro Gly Asp Pro
                 85                  90                  95

Asn Pro Arg Ser Ala His Met Gly Ser Ser Val Tyr Phe Ala Thr Pro
            100                 105                 110

Ser Gly Ser Leu Asn Thr Ser Asp Ser Gln Ile Phe Asn Arg Pro Tyr
            115                 120                 125

Trp Leu Arg Arg Ala Gln Gly Thr Asn Asn Gly Met Asp
            130                 135                 140

<210> SEQ ID NO 27
<211> LENGTH: 425
<212> TYPE: DNA
<213> ORGANISM: Papilloma virus

<400> SEQUENCE: 27
```

-continued

```
ggatccatgc cgttgttcgt tccttgagcc cgtcgtaacc aataaggtct gttaaatatt      60
tgtgaatcac tggtattaag ggagccacta ggtgttgcaa agtatactga agaacccata     120
tgagcgctcc tgggatttgg atctcctggt tttgcattta taaaatttac tccattagtc     180
tcattaggta ctggttctcc catagtacca gctctggcaa ataaatggcg agcataacat     240
tgctcgcgtt ttccaaagaa aaatacttca tttccataaa tatcctttgt catttttaga     300
aaatctggcc atatactaat actatctatt aattccagag gtacaccagc tctatcttgc     360
ataagcttag caaaattagc agcaccaaat cctatatcac ccatctcccc atcctctagg     420
gatcc                                                                 425
```

<210> SEQ ID NO 28
<211> LENGTH: 398
<212> TYPE: DNA
<213> ORGANISM: Papilloma virus
<220> FEATURE:
<221> NAME/KEY: CDS
<222> LOCATION: (1)...(396)

<400> SEQUENCE: 28

```
gga tcc ctt gag gat ggg gaa atg ata gat aca ggc tat ggt gcc atg      48
Gly Ser Leu Glu Asp Gly Glu Met Ile Asp Thr Gly Tyr Gly Ala Met
 1               5                  10                  15 gac ttt cgt aca ttg cag gaa acc aaa agt gag gta cca cta gat att      96
Asp Phe Arg Thr Leu Gln Glu Thr Lys Ser Glu Val Pro Leu Asp Ile
                20                  25                  30 tgc caa tcc gtg tgt aaa tat cct gat tat ttg cag atg tct gct gat     144
Cys Gln Ser Val Cys Lys Tyr Pro Asp Tyr Leu Gln Met Ser Ala Asp
            35                  40                  45 gta tat ggg gac agt atg ttt ttt tgt ttg cgc aag gaa cag ttg ttt     192
Val Tyr Gly Asp Ser Met Phe Phe Cys Leu Arg Lys Glu Gln Leu Phe
        50                  55                  60 gcc agg cac ttt tgg aat aga ggt ggc atg gtg ggc gac aca ata cct     240
Ala Arg His Phe Trp Asn Arg Gly Gly Met Val Gly Asp Thr Ile Pro
 65                  70                  75                  80 tca gag tta tat att aaa ggc acg gat ata cgt gag cgt cct ggt act     288
Ser Glu Leu Tyr Ile Lys Gly Thr Asp Ile Arg Glu Arg Pro Gly Thr
                85                  90                  95 cat gta tat tcc cct tcc cca agt ggc tct atg gtc tct tct gat tcc     336
His Val Tyr Ser Pro Ser Pro Ser Gly Ser Met Val Ser Ser Asp Ser
               100                 105                 110 cag ttg ttt aat aag ccc tat tgg ttg cat aag gcc caa ggc cac aat     384
Gln Leu Phe Asn Lys Pro Tyr Trp Leu His Lys Ala Gln Gly His Asn
           115                 120                 125 aac ggg atg gat cc                                                   398
Asn Gly Met Asp
       130
```

<210> SEQ ID NO 29
<211> LENGTH: 132
<212> TYPE: PRT
<213> ORGANISM: Papilloma virus

<400> SEQUENCE: 29

```
Gly Ser Leu Glu Asp Gly Glu Met Ile Asp Thr Gly Tyr Gly Ala Met
 1               5                  10                  15

Asp Phe Arg Thr Leu Gln Glu Thr Lys Ser Glu Val Pro Leu Asp Ile
                20                  25                  30

Cys Gln Ser Val Cys Lys Tyr Pro Asp Tyr Leu Gln Met Ser Ala Asp
            35                  40                  45
```

-continued

```
Val Tyr Gly Asp Ser Met Phe Phe Cys Leu Arg Lys Glu Gln Leu Phe
    50                  55                  60

Ala Arg His Phe Trp Asn Arg Gly Gly Met Val Gly Asp Thr Ile Pro
65                  70                  75                  80

Ser Glu Leu Tyr Ile Lys Gly Thr Asp Ile Arg Glu Arg Pro Gly Thr
                85                  90                  95

His Val Tyr Ser Pro Ser Pro Ser Gly Ser Met Val Ser Ser Asp Ser
            100                 105                 110

Gln Leu Phe Asn Lys Pro Tyr Trp Leu His Lys Ala Gln Gly His Asn
        115                 120                 125

Asn Gly Met Asp
    130

<210> SEQ ID NO 30
<211> LENGTH: 398
<212> TYPE: DNA
<213> ORGANISM: Papilloma virus

<400> SEQUENCE: 30
ggatccatcc cgttattgtg gccttgggcc ttatgcaacc aatagggctt attaaacaac      60
tgggaatcag aagagaccat agagccactt ggggaagggg aatatacatg agtaccagga    120
cgctcacgta tatccgtgcc tttaatatat aactctgaag gtattgtgtc gcccaccatg    180
ccacctctat tccaaaagtg cctggcaaac aactgttcct tgcgcaaaca aaaaaacata    240
ctgtccccat atacatcagc agacatctgc aaataatcag gatatttaca cacggattgg    300
caaatatcta gtggtacctc acttttggtt tcctgcaatg tacgaaagtc catggcacca    360
tagcctgtat ctatcatttc cccatcctca agggatcc                            398
```